(12) United States Patent
Kaufman

(10) Patent No.: US 6,288,045 B1
(45) Date of Patent: Sep. 11, 2001

(54) EPITHELIAL CELL CANCER DRUG

(75) Inventor: Harvey Kaufman, Hudson, OH (US)

(73) Assignee: Lifelink Pharmaceuticals, Inc., Stow, OH (US)

( * ) Notice: Subject to any disclaimer, the term of this patent is extended or adjusted under 35 U.S.C. 154(b) by 0 days.

(21) Appl. No.: 09/591,701

(22) Filed: Jun. 9, 2000

(51) Int. Cl.$^7$ ............................. C07F 7/02; A61K 31/695
(52) U.S. Cl. ................................. 514/63; 556/173
(58) Field of Search ................. 514/63; 556/173

(56) References Cited

U.S. PATENT DOCUMENTS 4,017,599 * 4/1977 Rubino ........................... 424/47

FOREIGN PATENT DOCUMENTS

| 19755921 | 6/1999 | (DE) . |
| WO 99/30580 | 6/1999 | (WO) . |

\* cited by examiner

*Primary Examiner*—Peter O'Sullivan
(74) *Attorney, Agent, or Firm*—George W. Moxon, II; Brouse McDowell

(57) ABSTRACT

A method of treating epithelial cell cancer comprising administering to a mammalian patient diagnosed as having an epithelial cell cancer a therapeutically effective amount of 4,5 di-cyclo, disilico, dimagnesium, dialumino, oxyo, trihydrate, or its acetate, sulfate, hydrochlorate, or brominate salts. The composition is synthesized from a naturally occurring non-toxic zeolites, and has a 100% kill rate within 72 hours against buccal mucosa and ling squamous epithelial cell cancers. It is not cytoxic to healthy human cells.

19 Claims, 9 Drawing Sheets

(6 of 9 Drawing Sheet(s) Filed in Color)

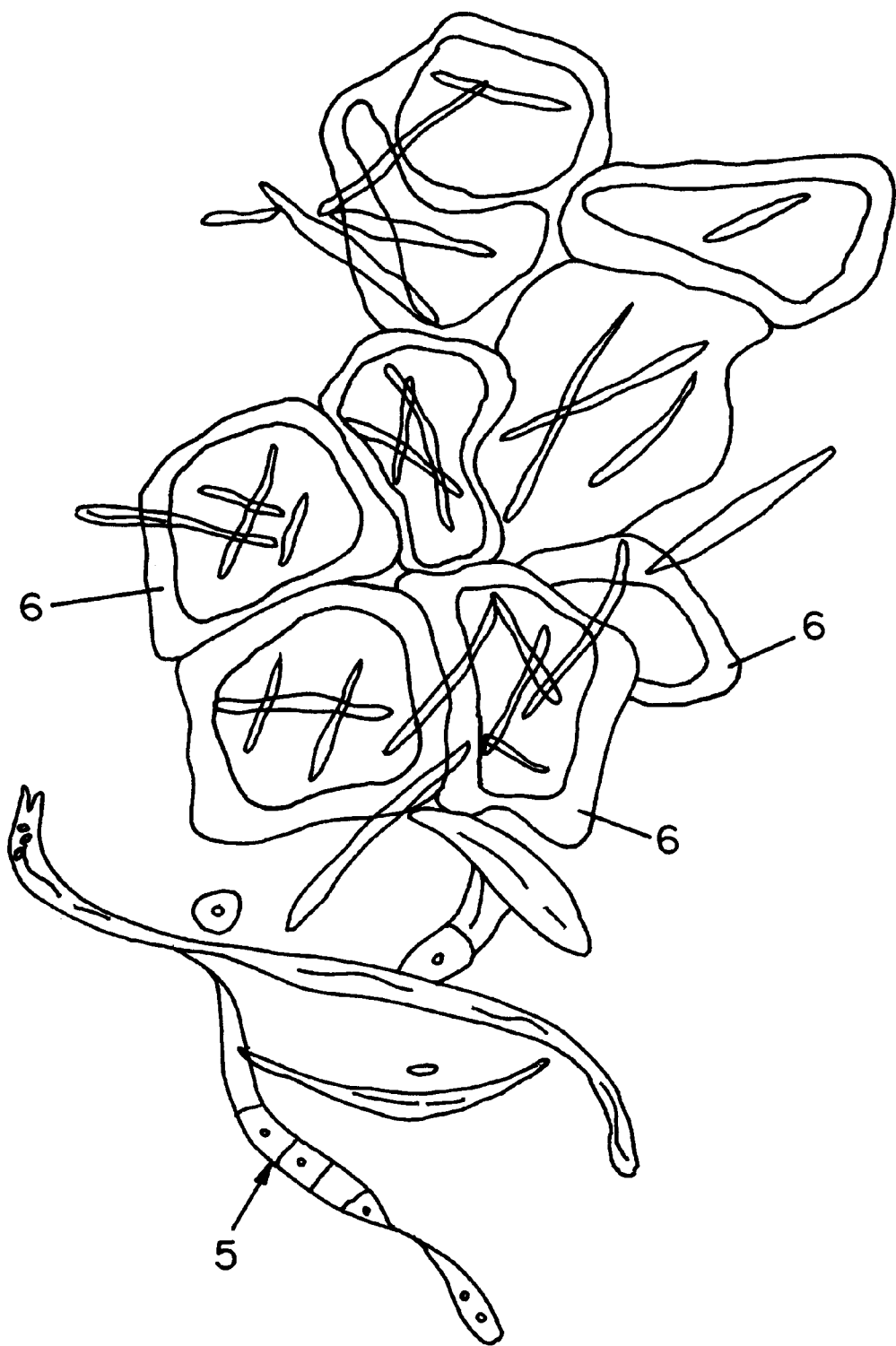
FIG. II

EPITHELIAL CELL CANCER DRUG

BACKGROUND OF THE INVENTION

The present invention is directed to a new and unique anticancer drug, which is identified generically as 4,5 di-cyclo, disilico, dimagnesium, dialumino, oxyo, trihydrate ($3Mg++.3Al_2O_3.3SiO_2.3H_2O$), which is a magnesium aluminosilicate (referred to hereinafter as "MAS"), and which are in the acetate, sulfate, chloride, or brominate form. These compositions come from a class of inorganic aluminosilicate chemicals known as zeolites. The compounds of the present invention are particularly useful in treating epithelial cell cancers in mammals.

The involvement of cancerous epithelial cells, which lead to the formation of solid tumors in humans, in such organs as the lungs, breast, skin, mouth, and colon are known as carcinomas. Most of the epithelial cell cancers are treated using chemotherapeutic agents and these tend to be toxic, and have immunosuppressive side effects. When treated this way, the cancer patient must then wait up to 3 weeks for his next treatment, until his immune system has restored itself.

Cancers involving human epithelial cells come from solid tumors of the breast, lung, stomach, liver, uterus, colon, skin, mouth and uterine cervix can form. Adenocarcinomas from secretory tissue and squamous carcinomas from protective linings are the two basic categories of carcinomas. Epithelial cell based cancers proliferate rapidly respecting no cellular boundaries. To fully understand how to treat epithelial cell based cancer, one must start at the cellular level, this involving use of cell culturing techniques. Present day drugs used for chemotherapy do not directly attack the cancer cell with any great accuracy. Drugs such as Methotrexate and Vincristine are toxic to normal healthy cells and diminish immune system functions. These usually offer the cancer patient extremely disquieting side effects such as diarrhea, hair loss, vomiting and weakness. The toxicity of these drugs often shorten their use or require a very intermittent use. The average chemotherapy cannot be used more than once a month.

A large effort has been put forth by the medical research community to find new drugs for the treatment of epithelial cell based cancers. Carcinoma of the lung, breast, prostate, and colon all together account for more than half of the deaths from cancer in North America. Anticancer drugs have for the most part been categorized into alkylating agents such as cytoxan, antitumor antibiotics such as dactinomycin and antimetablite drugs such as methotrexate. Most, if not all, of these chemotherapies have major side effects and are toxic.

It is well known that chemicals cause 95% of all cancers contracted by humans. Some of the most potent carcinogens are aldehydes, ketones, pyrenes, benzpyrenes, benzene, and nitrosamines. Nitrosamines were looked at early on because they are carcinogenic agents found in cigarette smoke and in the causative agents of rubber polymers.

Zeolites are natural hydrated silicates of aluminum and, usually, either sodium or calcium or both. Zeolites such as sodium aluminosilicate have a unique multi-dimensional structure of cavities into which small to medium size molecules and cells can be trapped. They exist in natural and artificial forms and are used extensively for water softening, as detergent builders, and cracking catalysts. Natural zeolites include analcite, chabuzite, heulandite, natrolite, stilbite, and thomosonite.

Zeolites have been used in animal feed. For example, as reported in "World Food & Drink Report", Apr. 19, 1990, hydrated sodium calcium aluminosilicate, an anti-caking agent used in animal feed, may reduce levels of aflatoxin in the milk of animals eating contaminated grain. Further, German patent DE19755921 teaches the use of zeolites or klinopitolites, that are used as food additives for human consumption as an aid to health, after they are treated with tribomechanical action to increase their surface area and destabilize their structure to release their chemical potential. These materials are thought to be a useful defense against cancers such as lung cancer, cancer of the colon, and skin cancer, and they are recommended for improving blood circulation.

SUMMARY OF THE INVENTION

The present invention has resulted from the discovery that epithelial cell cancer can be treated by administering to a mammalian patient having an epithelial cell cancer a therapeutically effective amount of 4,5 di-cyclo, disilico, dimagnesium, dialumino, oxyo, trihydrate acetate, sulfate, hydrochlorate, or bromate. The composition of the present invention is synthesized from a naturally occurring non-toxic zeolites, and has a 100% kill rate within 72 hours against buccal mucosa and ling squamous epithelial cell cancers. It is not cytoxic to healthy human cells.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 10 and 11 are illustrations showing cancerous gall pin oak leaf cells.

DETAILED DESCRIPTION OF THE INVENTION

Figure 1:
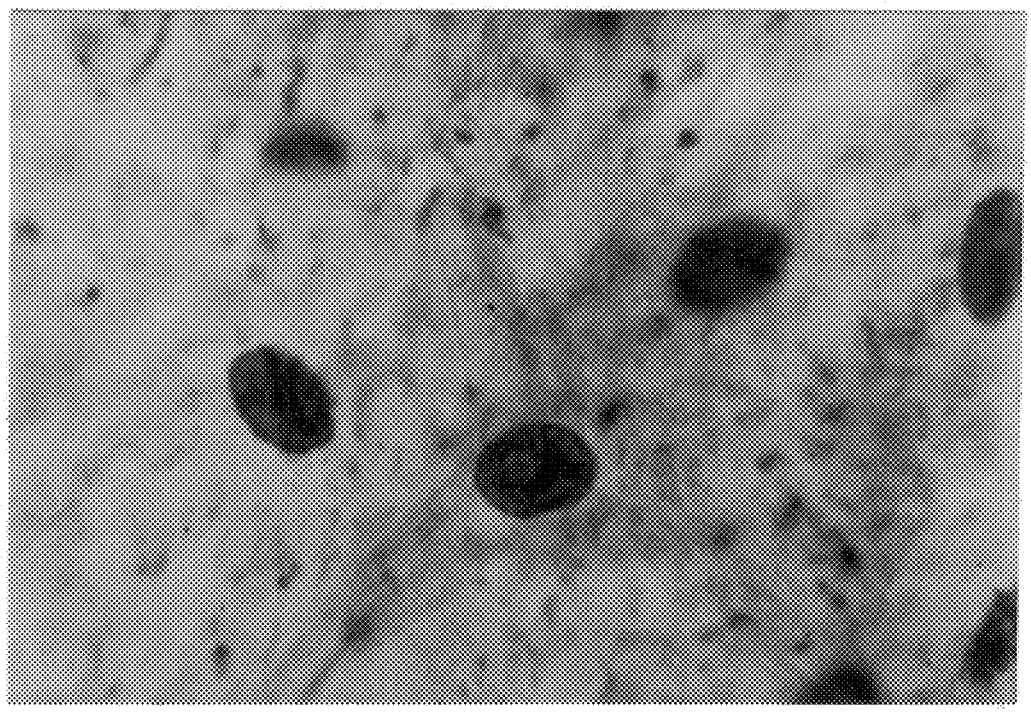
FIG. 1 is a photomicrograph of stained cells showing vacuoles containing the composition of the present invention prior to being brought into the cancer cells.

The composition of the present invention is 4,5 di-cyclo, disilico, dimagnesium, dialumino, oxyo, trihydrate ("MAS") salt synthesized from zeolites. It is used in its acetate, sulfate, hydrochlorate, or bromate salt forms. Zeolites are generally recognized as safe for humans. When these zeolites are converted and reacted with acetates, chlorides, sulfates, bromides, or gluconates the resultant product is a 4, 5, and 6-sided network of cavities holding anions and cations. The composition of the present invention has a molecular weight (weight average) of 1500 putting it into the polymer family.

The starting zeolite is sodium magnesium aluminosilicate. Preferably Hydrex R which is available from J. M. Huber Corporation. Alternatively it could be a zeolite such as Thomsonite, where magnesium is substituted for the calcium. It is processed by reacting the zeolite starting material with an acid, such as a 5 molar glacial acetic, hydrochloric, sulfuric, hydro-bromic or gluconic acid, preferably at 1 milliliter per 250 milliliters of hypotonic saline solution, in the presence of a poloxy compound, such as iron oxide $Fe_2O_3$ being preferred), calcium oxide, or sodium oxide, with iron oxide being preferred, at an amount of between about 0.0001 and 0.005% by weight with 0.003% by weight being preferred. The ratio of the mixture of the zeolite and the acid will preferably be about 30% by weight of a zeolite with 70% by weight of the acid, at 5% concentration, although it could be in a range of about 20 to 40% by weight of zeolite and 80 to 60% of acid. The reaction takes about two hours at a temperature of about 200 to 250° F.

Synthesis of the MAS

The synthesis of the new drug was carried out in a 500-milliliter three neck reaction flask, fitted with a stirrer, thermometer and cold water condenser apparatus. The zeolite starting material was Hydrex R, a sodium magnesium alumino silicate in an amount of 150 grams, available from the J. M. Huber Corporation. The amount of a 5 molar acid was 350 grams, and the iron oxide compound was 1.5 grams. The starting ingredients were combined and were reacted at 250 C for 2 hours followed by cooling. The acid was sulfuric acid at 1 milliliter per 250 milliliters of hypotonic saline solution. The final product was then diluted by adding twice as much sterile water and filtered via sterile millipore filtration apparatus. Quality control, and characterization of the compound was done using derivatization techniques, ASTM 3526, paper chromatographic analysis, molecular weight studies, and various wet bench analytical techniques. The average concentration of the drug of the present invention was 98 MG per milliliter of water.

In order to see if the composition of the present invention had any biological activity or "kill power" against the harshest microorganisms known, including streptococcus, staphylococcus, bacillus, fungus, and mildews, the microorganisms were cultured in RPMI 1640 cell culture media and in a starch-based, solid matrix culture media. All of these microorganisms were destroyed and also prevented from growing when first initiated with the patent substance. Thus the new composition of the present invention has been found to be bacteriostatic and bacteriocidal, fungistatic, and fungicidal, and a mildewicide.

The composition has a structure as follows:

Formula I

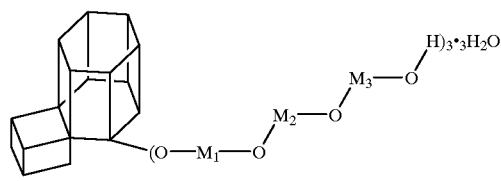

wherein $M_1$ is silicon, $M_2$ is magnesium, and $M_3$ is aluminum.

The drug must be administered directly into the cancer tumor by injection or a 24-hour intravenous slow drip. The patent substance must be in close proximity to or infused into the cancer cells and/or in the blood stream supplying the tumor. The precise amount dosed will vary and does not appear to be critical as long as it is pharmaceutically effective. Usually, this will be in the range of from about 0.001 to 1000 milligrams, with between about 20 and 300 being preferred.

The method of the invention can be practiced on any mammal having a susceptible cancer, i.e., a malignant cell population or tumor. Compounds of the invention are effective on human tumors in vivo as well as on human cell lines in vitro. The present compounds may be particularly useful for the treatment of solid tumors for which relatively few treatments are available. Such tumors include epidermoid and myeloid tumors, acute or chronic. Such tumors also include, nonsmall cell, squamous, liver, cervical, renal, adrenal, stomach, esophageal, oral and mucosal tumors, as well as lung, ovarian, breast and colon carcinoma, and melanomas (including amelanotic subtypes). The present compounds can also be used against endometrial tumors, bladder cancer, pancreatic cancer, lymphoma, Hodgkin's disease, prostate cancer, sarcomas and testicular cancer as well as against tumors of the central nervous system, such as brain tumors, neuroblastomas and hematopoietic cell cancers such as B-cell leukemia/lymphomas, myelomas, T-cell leukemia/lymphomas, small cell leukemia/lymphomas, as well as null cell, sezary, monocytic, myelomonocytic and Hairy cell leukemia. These leukemia/lymphomas can be either acute or chronic.

While not wishing to be bound by a particular theory, the composition of the present invention can react, or chelate into a complex, with carcinogenic agents. The basic chelation, or complexing ability of the $Mg^{++}$, (magnesium ions), O, (oxygen atoms) and aluminum ions which are inside the six (6) sided cavity of the zeolite composition of the present invention. This complexation now ties up the nitrogen to nitrogen to oxygen portion of the nitrosamine (—N—N—O) and prevents it from being metabolically activated by human liver enzymes inside cells to become the nitrous free radicals which then enter the healthy human cells nucleus, damaging the DNA of the chromosome and producing a rogue cell or cancer cell. The complexing of these carcinogenic nitrosamines was proven by using ASTM 3526 pager chromatography.

Figure 2:
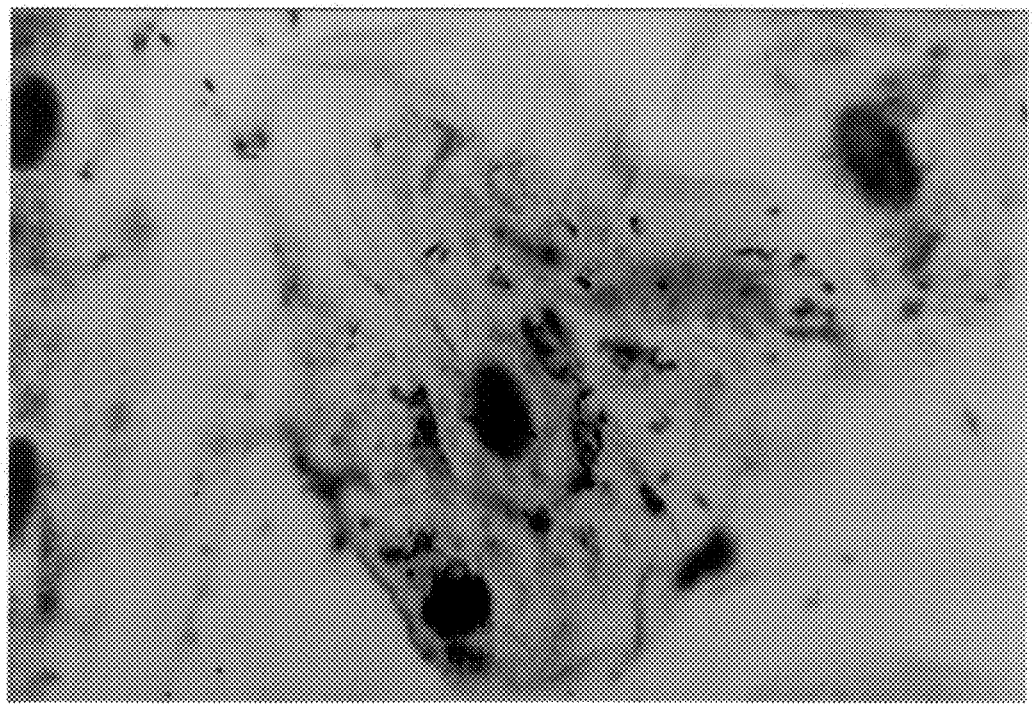
FIG. 2 is a photomicrograph showing the transition of vacuoles containing the new drug composition into the cancer cells.
Figure 3:
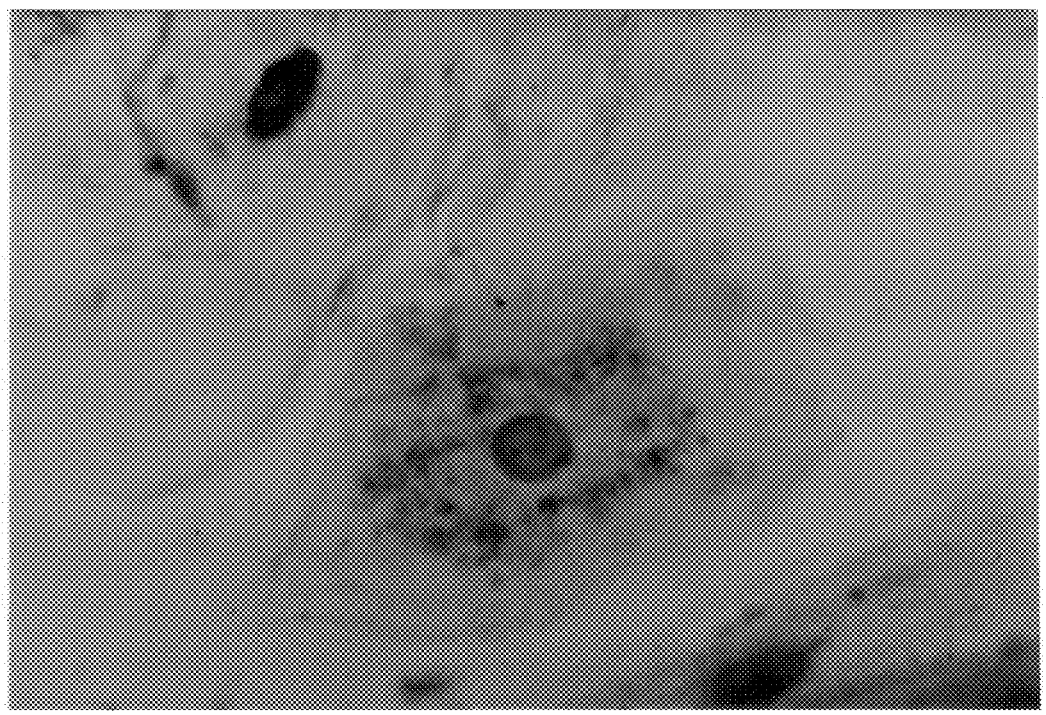
FIGS. 3–6 are photomicrographs showing the transition of the new drug composition into the cancer cells.
Figure 4:
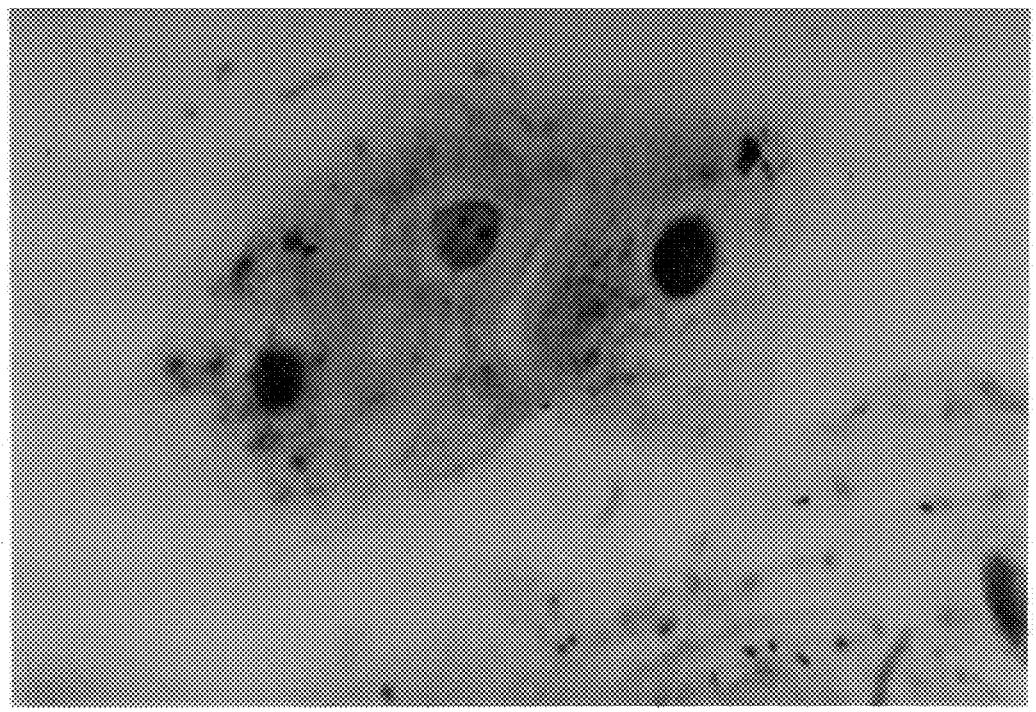
Figure 5:
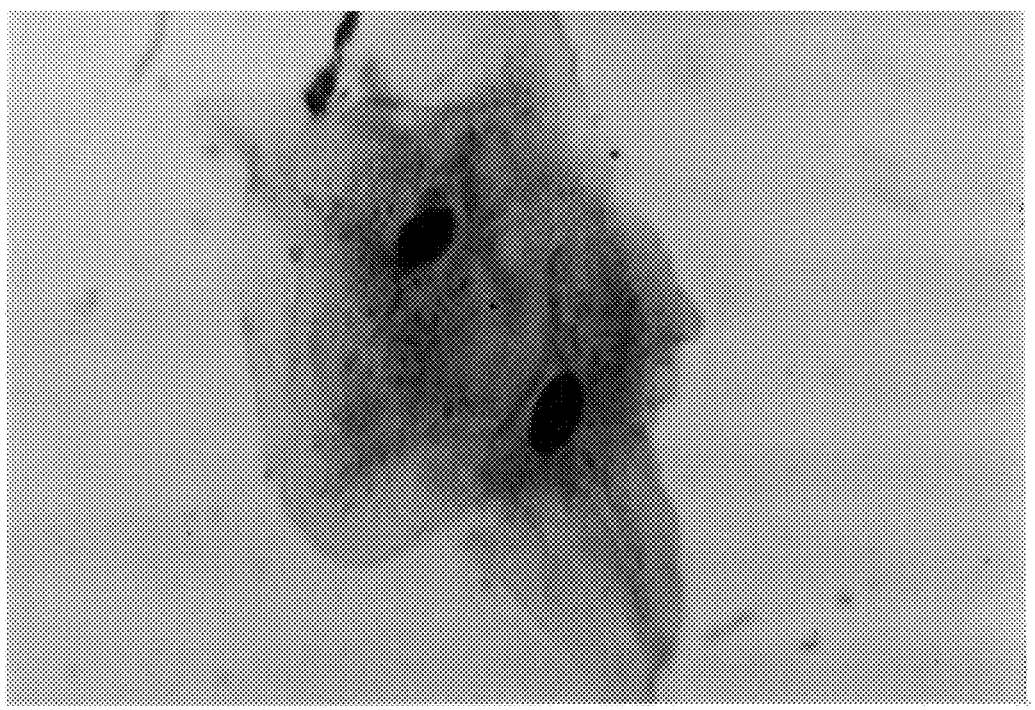
Figure 6:
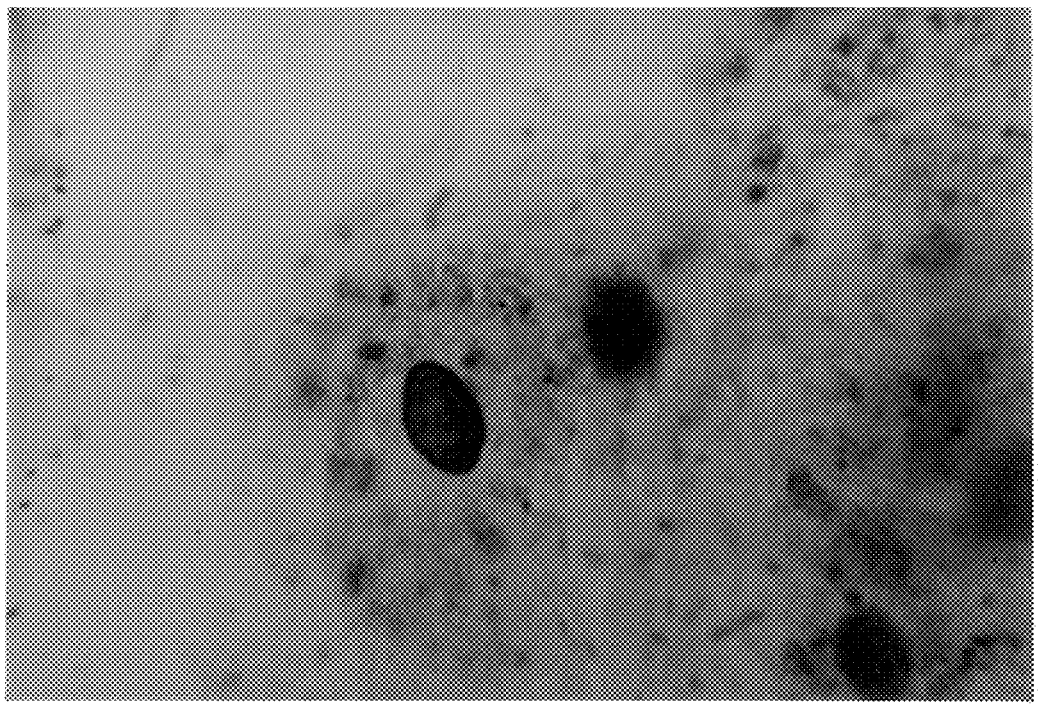

The compounds of the present invention target the cancerous epithelial cells, only, due to the different surface chemistry of the cancer cell itself Photomicrographs FIGS. 1 and 2, under X1000 oil immersion, show the formation of vacuoles containing MAS, which are prior to being brought into the cancer cell by endocytosis. Once inside, lysosomes attach and chemical breakdown of the MAS. The trimetallic portion of the MAS molecule crosses the nucleus of the cancer cell intercalates with the cell mutated DNA and destroys the cancer cell from within.

The formulations disclosed within the terms of the present invention may also comprise any additives, carriers, or fillers commonly in usage with drugs to facilitate their delivery.

The following examples are illustrative of the present invention, and should not limit the scope of the invention.

EXAMPLE 1

The following experiment was for the purpose of demonstrating the functionality of the compounds of the present invention with respect to carcinogenic compounds.

Ten (10) grams of a cured natural rubber compound were cut up to act as a control. This natural rubber compound contained 2 rubber additives which are known to generate nitrosamines; N-t-Butyl-2-benzothiazyl sulfonamide and zinc dimethyldithiocarbonate. Another 10 grams of this natural rubber compound, the same compound, contained 0.25 parts per hundred of the composition of the present invention. Both of the samples were extracted with warm acetone for 20 minutes, then cooled and the acetone carefully evaporated off. The remaining solids were dissolved in 0.5 ml of acetone and spotted in a paper chromatogram according to ASTM 3526. A 95% acetone, 5% ethyl acetate solvent system was employed. As can be seen in Table 1, the control generated nitrosamine at Rf (retention time) of 0.037. The composition of the present invention, at 0.25 pHR gave no nitrosamine fraction at 0.037, but the large, (high molecular weight) complex was at the origin or Rf=0, retention time 0. The nitrosamine was complexed by the patent substance and thus was made non-mutagenic, and non-carcinogenic.

TABLE 1

| Sample | Rf | Fraction |
| --- | --- | --- |
| Cured Natural Rubber Compound | 0.037 | Nitrosamine |
| " | .0448 | Trace Santocure NS |
| " | 0.761 | Trace Methasan |
| " | 0.970 | Process Oil |
| Cured Natural Rubber Compound plus 0.25 phr of MAS | 0 | Nitrosamine |
| Cured Natural Rubber Compound plus 0.25 phr of MAS | 0.492 | Trace Santocure NS |
| Cured Natural Rubber Compound plus 0.25 phr of MAS | 0.716 | Trace Methasan |
| Cured Natural Rubber Compound plus 0.25 phr of MAS | 0.940 | Process Oil |

EXAMPLE 2

Over a three (3) year period of study, oral cavity epithelial cells were obtained from buccal mucosa harvests from a single source. The cells were immediately placed in RPMI 1640 medium, which is a standard medium developed at the Roswell Park Memorial Institute. The medium was supplemented with L-glutamine, penicillin and streptomycin in all cultures, and then incubated at 98.6 F. The study cultures were supplemented with a carcinogen and strong promoter, sodium or magnesium saccharin. The sodium form being preferred. The cultures were incubated for 120 hours with one medium change for the extended time cultures. The sterile solutions of sodium or magnesium saccharin were made to a strength of 250 milligrams per milliliter of hypotonic saline solution, the combination penicillin-streptomycin antibiotic system were used at 100 units per milliliter of hypotonic saline solution.

The carcinogen-promoter supplemented cell cultures, also incubated at 98.6 C, once producing cancerous epithelial cells were given 300 microliter additions of the 4,5 sided ring MAS sulfate having concentrations of 60 milligrams per milliliter of hypotonic saline solution. Slides were prepared at room temperature using giemsa stain and observed and analyzed using bright field microscopy up to X1000 magnification with photomicrographs taken by the Polaroid Microcam System.

Phase contract microscopy at X100, and X200 power was also used, with photographs taken by the Polaroid Microcam System. All solutions used were sterilized via filtration. All cell counts were done on grided 2 chamber, cell culture slide chambers.

The epithelial cells used were obtained from sterile "Buccal Smears" of human cheek cells and were placed in sterile RPMI 1640 cell cultures with and without the composition of the present invention. The concentration of sodium saccharin used to promote the epithelial cell human cancer was 300 microliters of a 5 gram per milliliter working solution. All in-vitro, cell cultures were analyzed over a 3 day period (72 hours). Cancerous-like changes were seen in these cell cultures within 8–16 hours, and all the cancer cells were killed before 72 hours had lapsed.

A microscopic view shows normal check cell morphology, nuclear size, cell wall and membrane capacity and growth clustering; no ghosting or other abnormal changes were seen. The results are dramatic cell changes due to the sodium saccharin introduction to the cell culture. Observation of these cell cultures at X400, and X100 showed very enlarged cell morphology, formation of enlarged, crescent shaped nuclei, cell wall membrane swelling, multi-nucleated cell areas, formation of elongated or hook type epithelial cells in large sheaths were observed, plus the very telling formation of abnormal protein growth "Blebs" seen on the outer cell wall of these cells. These are illustrated in photomicrographs, FIGS. 3 through 6.

Figure 7:
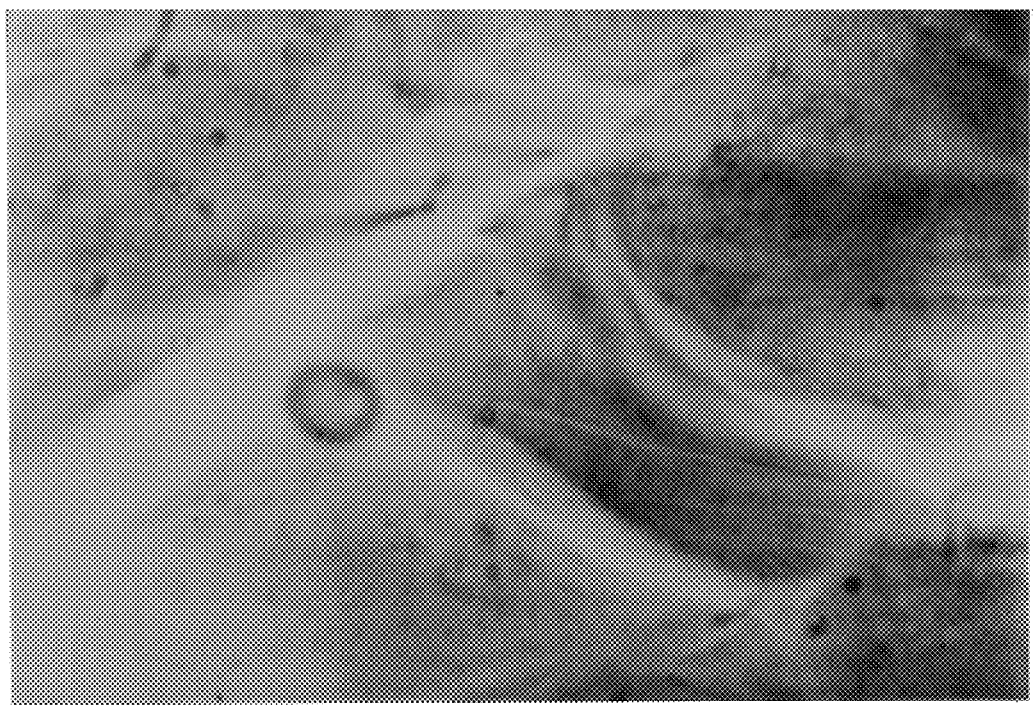
FIG. 7 is a photomicrograph showing the destruction of the cancer cells.

When the composition of the present invention is used as a non-toxic, anti-cancer agent in the cancerous epithelial cell cultures, at both 300 and 400 microliter dosages in these cell cultures, 100% epithelial cells induced to cancerous state were destroyed within 24 hours. This is shown in photomicrograph FIG. 7 by the "ghosting" or destruction of these cancer cells by the destruction of the cancer cell nucleus and cytoplasmic organelles. In some cases the cancer cells were destroyed in an outward burst of the cytoplasm by increased osmotic pressure. The composition of the present invention is totally amenable to the different receptor sites, cell wall membrane proteins, and surface chemistry of the cancer cell only. It does not effect ordinary, healthy cells as already shown and claimed above.

EXAMPLE 3

In this example, the plant cancer of study was the Pin Oak Tree Leaf Crown Gall plant cancer. The agrobacterium Tuma Faciens and its metabolites cause this well studied plant cancer. Normal leaf plant cells, and crown gall cancer cells were cultured in RPMI 1640 cell culture media, containing an antibiotic, and concentrations of the patent substance in its sulfate form. The average dosage of the patent substance was 300 microliters of a 98 milligram per milliliter concentration. Within 24–48 hours all cancer cells in the crown gall cell culture were dead as analyzed by Giensa stained microscope slides at X400, and X1000, power. The control cell culture of healthy pin oak leave section showed no cytotoxicity at all. The crown gall cells (cancer cells) were "ghosted" by the composition of the present invention.

The composition of the present invention crossed the cancer cell membrane, due to its different receptor site configuration and surface chemistry, destroyed the elongated nucleus and the cytoplasm bulged to one side of the cancer cell and the entire cellular contents dissipated into the surrounding environment. The membrane of most cells remained intact, but no cellular structures were left. Some cells were totally destroyed by cell wall and membrane collapse.

Figure 8:
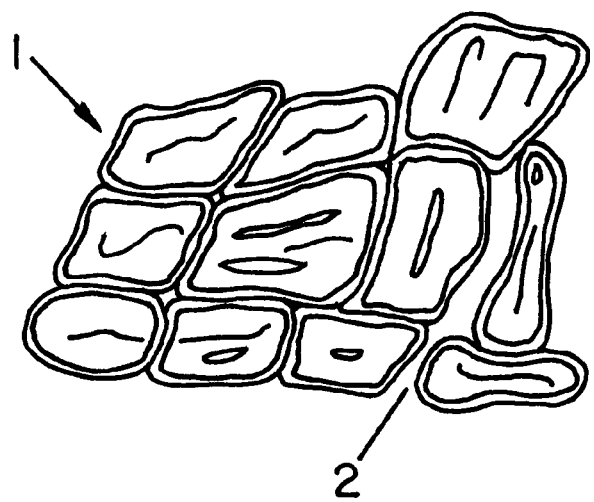
FIGS. 8 and 9 show illustrations of non-cancerous crown gall pin oak leaf cells.
Figure 9:
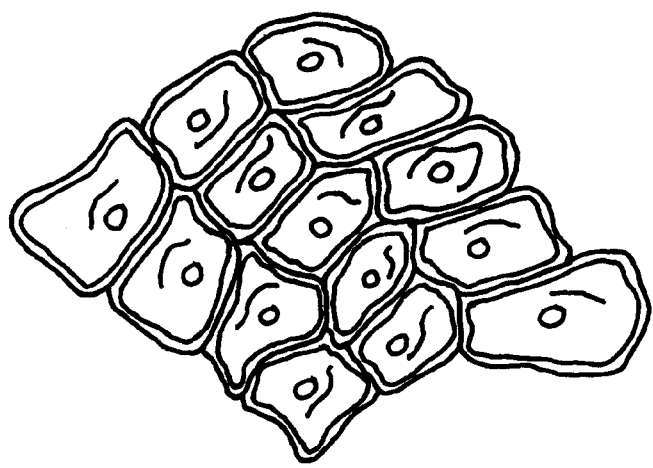
Figure 10:
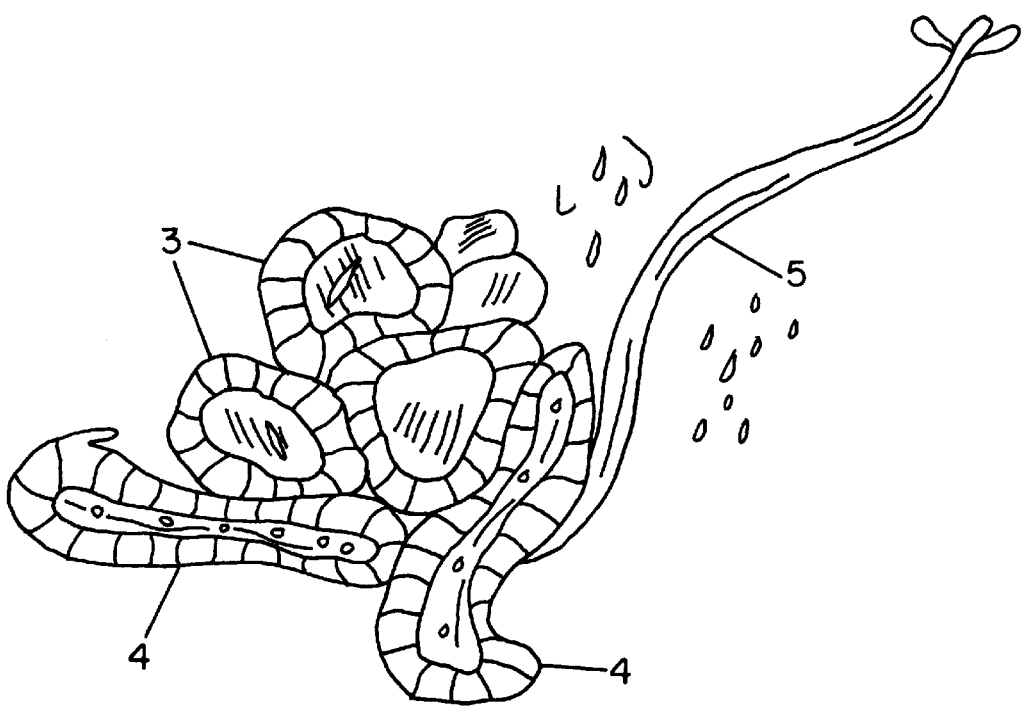
Figure 12:
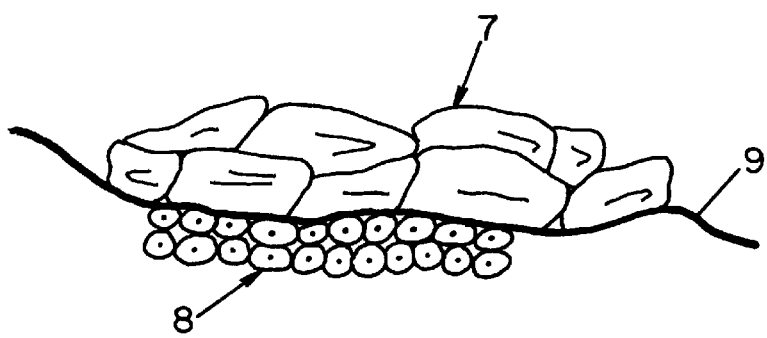
FIG. 12 is an illustration of crown gall pin oak leaf cells after treatment.
Figure 14:
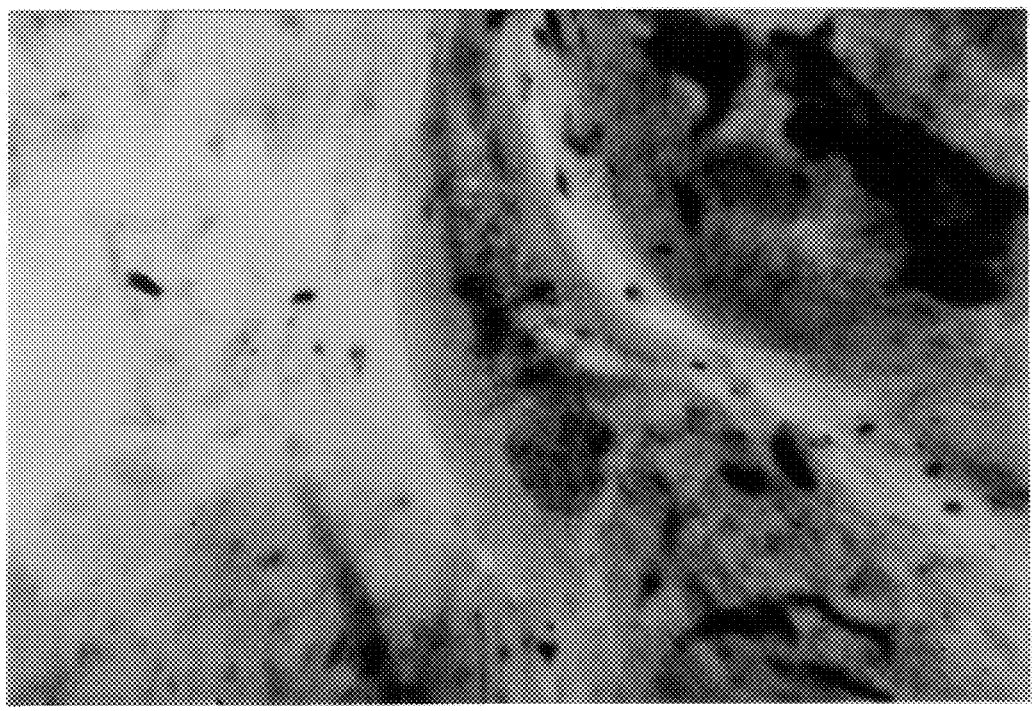
Figure 15:
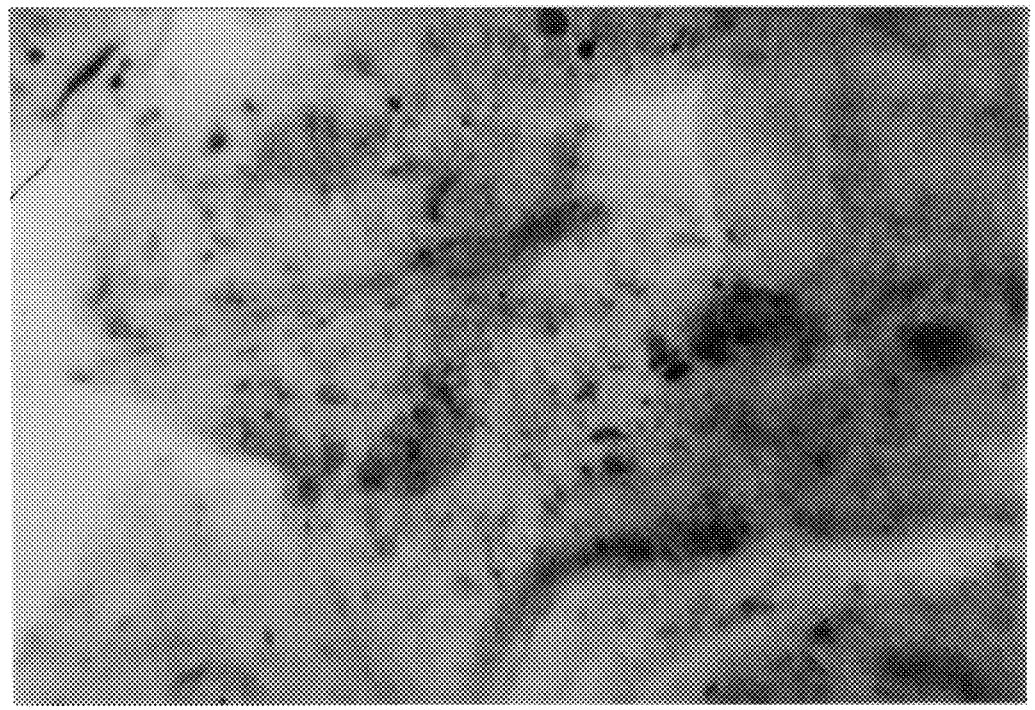
Figure 16:
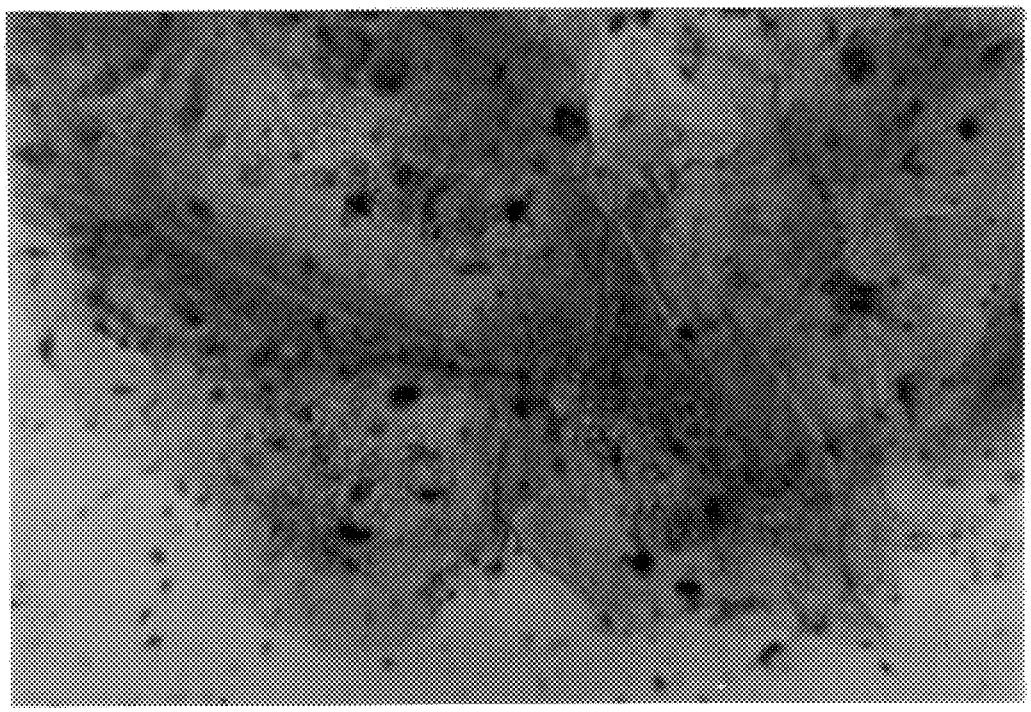
Figure 17:
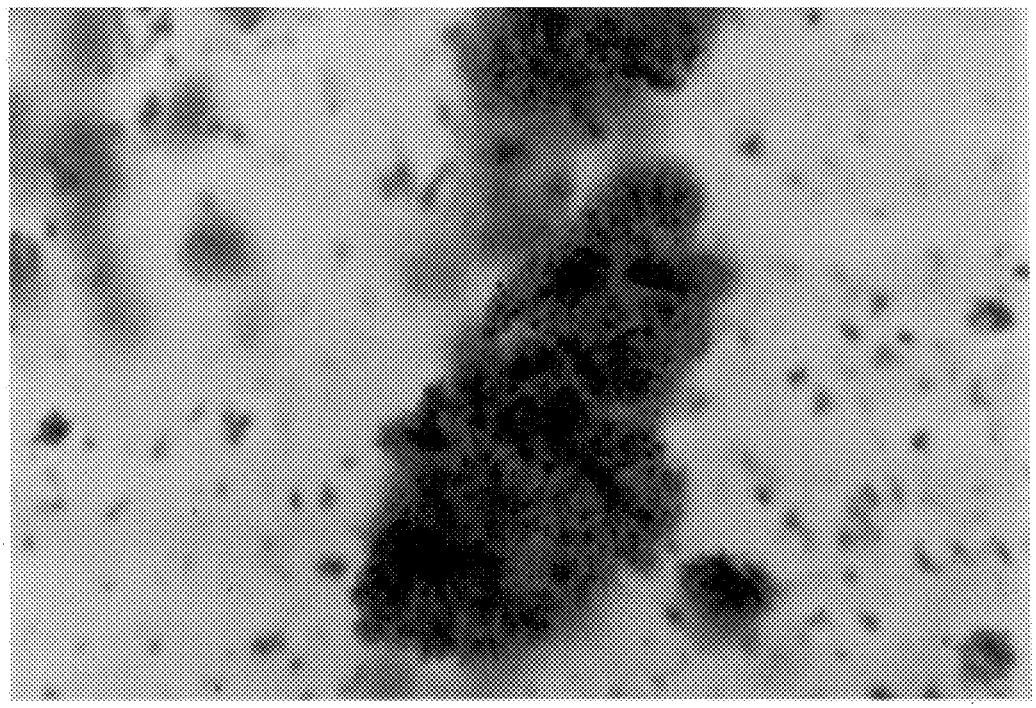

The healthy pin and cell cultures showed no ghosting, no elongated nuclear structure, or cell wall and membrane swelling. No extracellular growth or "Bleb" protein on the healthy cell wall, and membrane outer surface was noted. Usual cell counts were in the 300–500 cell range. FIGS. 8 and 9 show normal, non-cancerous (crown gall, non-cancerous) pin oak leaf cells. In FIG. 8, leaf section 1 is depicted with stoma 2. FIG. 9 shows normal non-cancerous crown gall pin oak leaf cells. FIGS. 10 and 11 show the pin oak crown gall cells, which are cancerous. FIG. 10 shows a cancerous cell in which has gel like, "eye" cells, 3, "hook" cells, 4, which are elongated, "nucleii" gels, and "ghosted" filiments, 5. FIG. 11 shows the enlarged cell membrane 6 as well as the filaments 5. FIG. 12 depicts crown gall pin oak leaf cells after treatment with 400 microliters of the composition of the present invention at 98 MG per milliliter. The xylem cells, 7, had some brownish color but no cellular damage. The lower cells were green, 8, below the boundary layer 9.

All cell culture preparations were done in sterile petri dishes with 25 milliters of RPMI 1640 cell culture media, and 100 microliters of antibiotic, cell counts ranged in member from 300–500, GIEMSA stained microscopic slides were prepared and observed at X400, and X1000. The concentration of composition of the present invention used was 300 and 400 microliters of a 98 MG per milliliter preparation.

EXAMPLE 4

Squamous cell human lung cancer cell cultures, which are commercially available as the A549 cell line from Bio-Whitaker Company, were cultured in RPMI 1640 Medium supplemented with L-glutamine, penicillin, and streptomycin. This culture was also incubated at 98.6° F., with cell culture times up to 96 hours, with at least one medium change. These cultures were also supplemented with doses of the drug of the present invention at 300 microliters of a concentration of 60 milligrams per milliliter of hypotonic saline solution. Fresh venous blood samples of 2 ml each were taken and placed in heparinized sterile test tubes for % hemolysis studies.

Figure 13:
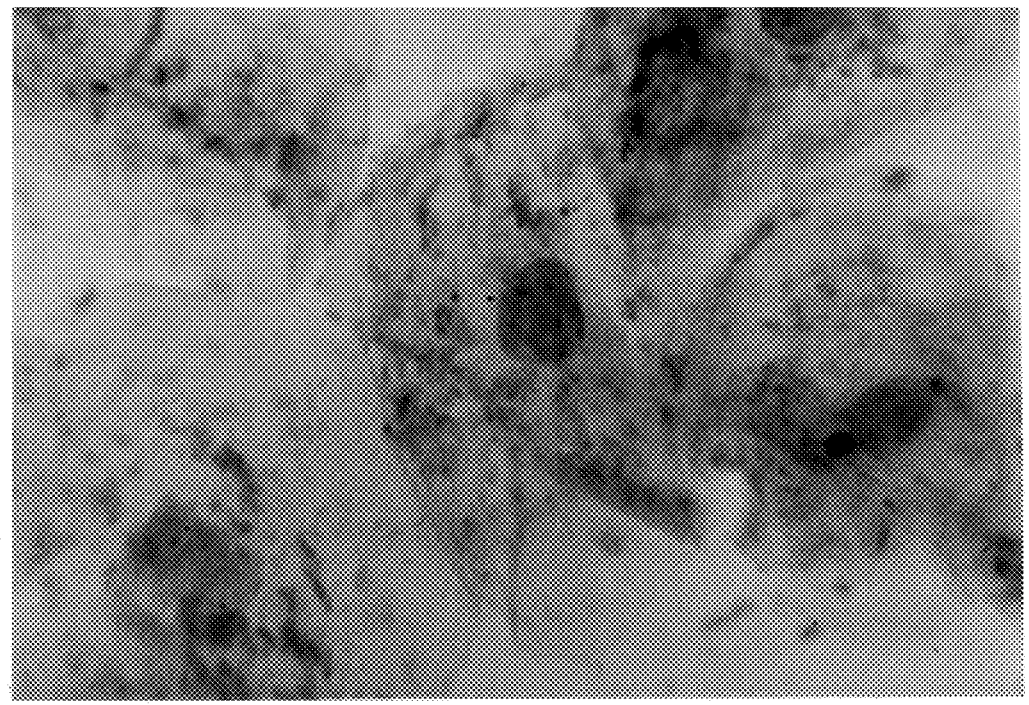
FIGS. 13–17 are photomicrographs of stained cells showing the progressive killing of the epithelial cancer by the drug composition of the present invention.

It has been shown that sodium saccharine or its magnesium counter is a weak carcinogen, but a strong promoter which increases the proliferation of epithelial cancer cells during cell cycling, over a three year period cell cultures of RPMI 1640 cells culture medium supplemented with L-glutamine and 100–200 microliters of penicillin and streptomycen each at 100 units per milliliter hypotonic saline solution, and dosed with 200–400 microliters of a concentrated solution of sodium saccharine (250 milligrams per milliliter of hyptotonic saline solution), incubated at 98.6° F., produced cancerous cells within 24–48 hours. Using phase contrast microscopy at X100, and X200 magnification and employing temporary slides for examination at X100, X400, and X1000 oil immersion magnification transitions from normal epithelial cells to well formed cancer cells could be cultured. In photomicrograph FIGS. 1, 7 and 13–14, giemsa stained cells and photographed at X1000 oil immersion magnification (using Polaroid microcam) we can easily see the transition of the healthy epithelial cells in photomicrograph FIGS. 1–3 to the transition of precancerous cells of photomicrographs FIGS. 4-6 where we observe a darkening of the cell cytoplasm, development of multinucleation, and a consistent swelling noted in the plasma membranes and large changes in cell morphology. Strikingly in photomicrographs FIGS. 7 and 13 we see the formation of oral cavity epithelial cells which have become cancerous in nature. We observe the proliferation of distorted cellular morphology to swollen, misshapen elongated, hook like cells, with thick fibrous cytoplasm and the growth of fibrous, abnormal proteins on the cells outer wall ('BLEBS'), multinucleation and nuclei that seem to elongate and become abnormal in shape, similar to the morphology changes of the cancer cell itself, are seen along a medial axis. A typical cell count of these cell cultures shows that the number of epithelial cells declines at the same rate as does the growth of the cancer cells, which result is shown by the data in Table 2. Normal control cultures lacking, the supplement of sodium saccharine, also incubated at 98.6° F. gave normal, healthy cell cultures of oral cavity epithelial cells. See photomicrograph FIGS. 1–3.

TABLE 2

Typical Cell Count Statistics After Introduction of Sodium Saccharine

| Time Hours | # of Normal Epithelial Cells | # of Transition Cells | # of Cancer Cells |
| --- | --- | --- | --- |
| T = 0 | 462 | 0 | 0 |
| T = 24 | 200 | 60 | 260 |
| T = 48 | 5 | 10 | 500 |

Over a three year period the cell cultures produced were treated with MAS Sulfate within 24–48 hours of the formation of epithelial cancer cells. Dosages of 100–400 microliters of MAS Sulfate at 60 milligrams per milliliter of drug were, and within 72 hours of addition, 100% of all epithelial cancer cells were destroyed, showing cell casts and/or entirely "ghosted" cells. In Table 3 we can see cell counts on a typical cell culture where MAS Sulfate was added. The photomicrographs were taken from giemsa stained slides at X100magnification, using oil immersion. Photomicrograph FIGS. 7 and 14–16 show the progressive killing of the epithelial cancer by MAS Sulfate. It will also be shown MAS Sulfate non-cytoxic to date.

TABLE 3

Data Obtained from a Hemolytic Titer of MAS Sulfate on Human Red Blood Cells

| Dilution of MAS Sulfate in 1000 Microliters Hypotonic Saline | % Hemolysis of Human Red Cells |
| --- | --- |
| 7.40 Microliters | 0 |
| 8.00 Microliters | 0 |
| 10.00 Microliters | 0 |
| 50.00 Microliters | 0 |
| 100.00 Microliters | 0 |
| 200.00 Microliters | 0 |
| 500.00 Microliters | 0 |
| 700.00 Microliters | 0 |
| 1000.00 Microliters | 1.99 |
| 2000.00 Microliters | 2.35 |

MAS Sulfate is not cytotoxic to these cells and preferentially target epithelial cancer cells only. A hemolytic titer study was done on the new drug to show non-cytotoxicity. Typical data obtained using human red cells shows the lack of cytotoxicity to cells. The concentration of MAS Sulfate used was 60 milligrams per milliliter of hypotonic saline solution. No hemolysis appears until 1 full milliliter of MAS Sulfate and then only 2.00% hemolysis. The next data point shows that at a concentration of 2.00 milliliters of MAS Sulfate only 2.50% hemolysis of red blood cells occurs. A concentration of 0.35 microliters of human red blood cells was used for each sample titer. Table 2 shows the titer data in graphic form exhibiting a flat line effect until the 1.00 milliliter sample of MAS Sulfate.

A close look at the cell count in Table 3 clearly shows the rapidity of MAS to selectively cross the epithelial cell (cancerous) plasma membrane, in cell culture experiments and provide 100% kill rates within relatively short time period (48 to 72 hours), in this case 1,090 cells counted at 48 hours after addition of a total of 300 microliters of MAS Sulfate at a concentration of 60 milligrams per milliliter hypotonic saline solution. Also MAS Sulfate shows a strong inhibitory action in reducing cell culture proliferation of the cancer cells to 0.82%. MAS Sulfate and its family of conjugate drugs are totally water-soluble such that by % hemolysis studies concentrations up to 120 milligrams, where red blood cell hemolysis is barely perceptible, can be tolerated.

By repeating these same experiments with a cell line of squamous cell lung cancers (BIO-WHITTAKER A549), similar results are achieved as seen in Table 4.

561–230 could possibly be cells experiencing normal cell death. In referring to Table 4, our cell cycle model, the transition cells increased in numbers after 48 hours, due to cells that were in the G1 cycle at the time of addition of the second dosage of sodium saccharin and only partially affected by the first dosage. As seen in Table 4, cancer cell counts reflect the total affect of the cells being exposed to the X2 dose of the sodium saccharin. The cells have transformed into transition (pre-cancer cells) and cancer cells within 24 to 48 hours after inoculation. The first sign of cancer cells

TABLE 4

Quantitative Cell Culture of Human Buccal Mucosa Epithelial Cells

| Time (AGG) of Culture | Time of DME Add | Vol. Sodium Saccharin | Vol. DME ML | Total Cells | # Normal Cells | # Transition Cells | # Cancer Cells | # Dead Cancer cells | # Cell Growth | % Increase Cell Growth |
|---|---|---|---|---|---|---|---|---|---|---|
| 0 | — | 200 ML | — | 463 | 463 | 0 | 0 | 0 | 0 | 0 |
| 24 | — | — | — | 661 | 561 | 68 | 32 | 0 | 198 | 42.76 |
| 48 | — | 100 ML | — | 749 | 230 | 200 | 319 | 0 | 88 | 13.31 |
| 72 | — | — | — | 805 | 60 | 45 | 700 | 0 | 56 | 7.48 |
| 96 | — | — | — | 873 | 3 | 10 | 860 | 0 | 68 | 8.45 |
| 120 | 0 | — | 100 | 1020 | 0 | 0 | 1020 | 0 | 147 | 16.84 |
| 144 | 24 | — | 200 | 1081 | 0 | 0 | 250 | 831 | 61 | 5.98 |
| 168 | 48 | — | — | 1090 | 0 | 0 | 0 | 1090 | 9 | 0.82 |

It has been seen that pre-cancerous and cancerous cells have extremely different cellular characteristics and surface cell chemistry than normal cells. Predominantly amongst these characteristics are the gross morphological changes of the cancerous epithelial, lack of yet totally unknown plasma membrane protein growths familiarly known as 'BLEBS,' changes in numbers of and mutations in receptor sites such as the EFG, and VEG F receptor sites controlling cell cycle functions. Proteolytic enzymes and increased lysosomal activity are also important changes in the cytoplasm of these cells. It has been seen during our research studies that the MAS molecule itself is transported, selectively across the cancerous epithelial cell membrane and once in the environs, crosses the nuclear membrane and deactivates cancer cell replication by action on the mutated DNA. Then, with the collapse of the nucleus osmotic pressure within the cancer cell ruptures the plasma membrane outwardly. Photomicrograph FIGS. 1–7 and 13–16 show these cancer cell "casts" and "ghosted" cytoplasms of our treated epithelial cancer cells within the time of 48 to 72 hours as seen in Table 4. Referring to Table 4, the number of cancer cells here represent cells in G2 or late S phase at the time of introduction of the sodium saccharin, (all additions of sodium saccharin and MAS Sulfate were added after cell counts were taken). They were affected by the sodium saccharin to cause cancer as early as 24 hours after inoculation. The transition cell's morphology may represent affects of the sodium saccharin to cells in the early S phase of the cell cycle from the time of inoculation to the time of cell count at 24 hours. As seen in this data the number of normal cells seen after 24 hours of exposure to sodium saccharin represents cells safely in G2 phase of the cell cycle prior to the addition of the sodium saccharin. Referring to Table 4, normal cells seen after 48 hours in cell culture may represent cells that have survived in the culture unaffected by the sodium saccharin treatment the difference of the cell count after 24 hours is probably representative of cells in synthetic period of the cell cycle at the time of addition of the sodium saccharin. The rapid progression of cells to the transition state and consequently to the cancer cell state shows an aggressive division process that took place in the first 3–4 days in the cell culture. By the addition of the MAS Sulfate to the culture, there is a rapid demise of the cancer cell population after 24 hours and total cell death after 48 hours. The MAS Sulfate molecule, represented in Formula I selectively enters the cancer cell's plasma membrane.

It is the belief that this new pharmacological approach of selectively targeting cancer cells is a significant step in providing a new therapy, which is also non-cytoxic, for the treatment of carcinomas. The use of this drug will shorten the gap betweeen the number of patients getting cancer and a chemotherapeutic approach to saving lives. The ramifications of a substance which will target epithelial cancer cells selectively without harming normal tissue is overwhelming with regards to cancer treatment. Of ever greater significance, may be its ability to destroy transitional cells serving as a preventive agent in numerous clinical opportunities.

The drug of the present invention, in cell culture, effectively kills epithelial cell based cancers, at 100% "kill power" from the work presented. A patient could receive the new anticancer drug more than once every three weeks, perhaps several times a week.

The formation of cell wall membrane irregular proteins (Blebs) in these, nuclei as large as the cytoplasm, very differential cell morphology, some in shapes of hooks, others in large sheaths, and, formation of cell membrane swelling. It was also observed that the widespread deformation of these cancer cell nuclei are enlarged, crescent shaped, peanut shaped, and appear to be multi-nucleated in this study. The drug of the present invention was added to the known human cancer cell cultures and within 24–48 hours as 100% lower cancer cell kill was established. The cancer cells have been "ghosted", their nuclei and organelles destroyed from within. This allows for stopping-cancer cell division, decreasing tumor size, stopping cancer metastasis, and not effecting healthy cells, like t-cells in the human immune system. The composition of the present invention can be used as a cancer chemotherapy systemically via IV or directly infused into the tumor and made available to the cancer patient several times weekly.

EXAMPLE 5

A study was conducted using standard immunodeficient (SCID) mice. Some of the mice were injected with the standard A549 squamous cancer cell line, with the C.B-17/IcrCrl-scidBR strain being selected, while some of the mice were injected with the A549 cell line and MAS sulfate drug prepared in accordance with the present invention. The mice were divided into three groups:

Group I: Two mice were a control and were not treated with either the A549 cell line nor the MAS sulfate drug.
Group II: Four mice were treated with the A549 cell line, but not the MAS sulfate drug.
Group III: Four mice were treated with the A549 cell line and the MAS sulfate drug.

The A549 cell line dose was at $2.5 \times 10^6$ cells per milliliter. The MAS sulfate was dosed at 30 miligrams per injection, three times per week. The injections were in dorsal thorax area.

The animals were about six to seven weeks of age at the start of the test and their weight variation did not exceed ±20 percent of mean weight. The animals underwent a quarantine/acclimation period of five days prior to implantation with the A549 cells. The animals were handled in accordance with the "Guide for the Care and Use of Laboratory Animals", published by the Institute of Laboratory Animal Resources, Commission on Life Sciences, National Research Counsel, including environmental conditions, handling, storage and feeding.

The observations of the changes in the body weights are shown in Table 5, which shows expected weight gains.

TABLE 5

Body Weights in Grams

| Animals | Pretest Weight in Grams | Week 1 Weight in Grams | Week 2 Weight in Grams | Week 3 Weight in Grams | Week 4 Weight in Grams |
| --- | --- | --- | --- | --- | --- |
| Group I | | | | | |
| A | 21.4 | 22.8 | 23.7 | 25.1 | 25.8 |
| B | 21.5 | 22.8 | 23.8 | 25.4 | 26.2 |
| Mean Wt. | 21.5 | 22.8 | 23.8 | 25.3 | 26.0 |
| Group II | | | | | |
| A | 20.0 | 21.6 | 21.6 | 22.6 | 22.8 |
| B | 19.9 | 20.5 | 20.9 | 22.3 | 23.5 |
| C | 20.9 | 22.5 | 22.7 | 24.3 | 25.0 |
| D | 22.3 | 23.8 | 24.6 | 26.0 | 26.8 |
| Mean Wt. | 20.8 | 22.1 | 22.5 | 23.8 | 24.5 |
| Group III | | | | | |
| A | 20.7 | 22.4 | 22.1 | 23.3 | 24.5 |
| B | 21.9 | 23.4 | 23.5 | 24.5 | 25.6 |
| C | 21.8 | 23.3 | 23.2 | 24.7 | 25.2 |
| D | 21.0 | 22.5 | 22.5 | 24.0 | 24.3 |
| Mean Wt. | 21.4 | 22.9 | 22.8 | 24.1 | 24.9 |

At the end of the observation period of the study, which was approximately five weeks, the mice were humanely terminated using a standard procedure of carbon dioxide asphyxiation and opening the thoracic cavity or exsanguination. Necropsies were performed and tissues, namely liver, kidney, spleen, lung, and any other abnormal appearing tissue, were examined via histopathology. The results are shown as follows in Tables 6 and 7.

TABLE 6

Tumor Mass Measurements

| Animal | Week 2 L × W × H | Vol. | Week 3 L × W × H | Vol. | Week 4 L × W × H | Vol. | Week 5 L × W × H | Vol. |
| --- | --- | --- | --- | --- | --- | --- | --- | --- |
| Group I | | | | | | | | |
| A | No Mass | | No Mass | | No Mass | | No Mass | |
| B | No Mass | | No Mass | | No Mass | | No Mass | |
| Group II | | | | | | | | |
| A | 9 × 6 × 3 | 162 | 8 × 8 × 3 | 192 | 10 × 6 × 6 | 360 | 12 × 11 × 8 | 1056 |
| B | 9 × 7 × 3 | 189 | 10 × 5 × 3 | 150 | 14 × 8 × 4 | 448 | 15 × 10 × 9 | 1350 |
| C | 5 × 5 × 3 | 75 | 12 × 3 × 10 | 360 | 15 × 12 × 8 | 1440 | 20 × 14 × 5 | 1400 |
| D | 2 × 2 × 1 | 4 | 10 × 7 × 3 | 210 | 12 × 9 × 4 | 432 | 16 × 10 × 8 | 1280 |
| Mean | | 107.5 | | 228.0 | | 670.0 | | 1271.5 |
| Std Dev | | 84.4 | | 91.5 | | 514.8 | | 151.9 |
| Group III | | | | | | | | |
| A | 1 × 3 × 2 | 6 | 10 × 7 × 3 | 210 | 13 × 7 × 4 | 364 | 18 × 9 × 6 | 972 |
| B | 1 × 3 × 2 | 6 | 10 × 4 × 3 | 120 | 14 × 7 × 4 | 392 | 17 × 8 × 6 | 816 |

TABLE 6-continued

Tumor Mass Measurements

| Animal | Week 2 L × W × H | Vol. | Week 3 L × W × H | Vol. | Week 4 L × W × H | Vol. | Week 5 L × W × H | Vol. |
|---|---|---|---|---|---|---|---|---|
| C | 5 × 3 × 2 | 30 | 10 × 7 × 3 | 210 | 11 × 8 × 5 | 440 | 13 × 10 × 6 | 780 |
| D | 3 × 4 × 2 | 24 | 10 × 5 × 3 | 150 | 11 × 6 × 4 | 264 | 14 × 9 × 5 | 630 |
| Mean | | 16.5 | | 172.5 | | 365.0 | | 799.5 |
| Std Dev | | 12.4 | | 45.0 | | 74.3 | | 140.4 |

TABLE 7

Histopathology Incidence Table

| | Group I Animal | | Group II Animal | | | | Group III Animal | | | |
|---|---|---|---|---|---|---|---|---|---|---|
| | A | B | A | B | C | D | A | B | C | D |
| HEART | | | | | | | | | | |
| Epicardium, Mineralization | | | | | | | 2 | 3 | 3 | |
| KIDNEY | X | | | X | X | X | | X | X | C |
| Cortex, Tubules, Regeneration | | 1 | 1 | | | | 1 | | | |
| LACRIMAL GLAND | | | | | | | X | | | |
| LIVER | X | X | X | X | | X | | X | X | X |
| Hematopoiesis | | | | | 1 | | 1 | | | |
| LUNG | | | | | | | | | | |
| Alveolus, Hemorrhage | 1 | | 2 | 1 | 1 | 1 | 2 | 1 | | |
| Alveolus, Histiocytosis | | | 2 | | | | | | | |
| Peribronchial Lymphoid Depletion | 5 | 5 | 5 | 5 | 5 | 5 | 5 | 5 | 5 | 5 |
| LYMPH NODE, NOS | | | | | | | N | | | |
| SKIN/SUBCUTIS | | | | | | | | | | |
| Carcinoma, NOS | | | P | P | P | P | P | P | P | P |
| Adnexal Atrophy | | | 1 | 1 | | 1 | | 2 | | |
| Dermis, Fibrosis | | | 1 | | | | 1 | 2 | 1 | |
| Dermis, Inflammation, Chronic Active | | | 1 | 1 | | | | 2 | | |
| Epidermis, Erosion/Ulceration | | | 1 | 1 | | 3 | 1 | 2 | 1 | |
| Epidermis, Hyperplasia | | | 2 | 2 | | 2 | 2 | 2 | 2 | 1 |
| Epidermis, Inflammation, Suppurative | | | | | | | 2 | 2 | 1 | |
| SPLEEN | | | | | | | | | | |
| Hematopoiesis | 4 | 4 | 4 | 4 | 5 | 4 | 4 | 4 | 4 | 4 |
| Lymphoid Depletion | 5 | 5 | 4 | 4 | 5 | 4 | 5 | 5 | 5 | 5 |
| TESTIS | | | | | N | | | | | |

X = Not Remarkable
N = No Section
P = Present
Scale:
1 = Minimal
2 = Slight/Mild
3 = Moderate
4 = Moderately Severe
5 = Severe/High As seen in Table 6, the tumor mass in the mice that were not treated with the drug of the present invention was significantly higher than those that were treated. Further, the results in Table 7 show that for the spleen, the liver and the kidneys, no significant change occurred from the use of the drug of the present invention. Further, since mice are immunodeficient, the results were consistent with not dosing the mice with the cancer or the drug of the present invention.

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated. It is intended that the invention be defined by the following claims.

What I claim is:

1. 4,6 cyclo, trisilico, trimagnesium, trialumino, oxyo, trihydrate acetate.

2. 4,6 cyclo, trisilico, trimagnesium, trialumino, oxyo, trihydrate sulfate.

3. 4,6 cyclo, trisilico, trimagnesium, trialumino, oxyo, trihydrate hydrochlorate.

4. 4,6 cyclo, trisilico, trimagnesium, trialumino, oxyo, trihydrate brominate.

5. A composition consisting essentially of 4,5 di-cyclo, disilico, dimagnesium, dialumino, oxyo, trihydrate acetate, sulfate, chlorate, or brominate.

6. A pharmaceutical composition comprising a drug selected from the group consisting essentially of 4,5 cyclo, trisilico, trimagnesium, trialumino, oxyo, trihydrate acetate, 4,6 cyclo, trisilico, trimagnesium, trialumino, oxyo, trihydrate sulfate, 4,6 cyclo, trisilico, trimagnesium, trialumino, oxyo, trihydrate chlorate, and 4,6 cyclo, trisilico, trimagnesium, trialumino, oxyo, trihydrate brominate, and a pharmaceutically acceptable carrier.

7. The composition of claim 6 wherein said drug is present in an amount of between about 0.001 and about 1000 milligrams.

8. The composition of claim 6 wherein said drug is present in an amount of between about 20 and about 300 milligrams.

9. A cancer drug comprising the reaction product of a sodium magnesium aluminosilicate and an acid selected from the group consisting of glacial acetic, hydrochloric, sulfuric, hydro-bromic, and gluconic.

10. The composition of claim 9 wherein the reaction is conducted in the presence of a poloxy compound.

11. The composition of claim 10 wherein the poloxy compound is selected from the group consisting essentially of iron oxide, calcium oxide, and sodium oxide.

12. The composition of claim 9 wherein the reaction is conducted at a temperature of between about 200 and 250° F.

13. The composition of claim 9 wherein the silicate is present in an amount of 20 to 40% by weight of the mixture and the acid is present in an amount of about 80 to about 60% by weight of the mixture of the silicate and the acid.

14. The composition of claim 10 wherein the poloxy compound is present in an amount of between about 0.0001 and 0.005% by weight.

15. A method of treating epithelial cell cancer comprising administering to a mamalian patient diagnosed as having an epithelial cell cancer a therapeutically effective amount of a drug selected from the group consisting of 4,5 di-cyclo, disilico, dimagnesium, dialumino, oxyo, trihydrate acetate, sulfate, chlorate, and brominate.

16. The method of claim 15 wherein the drug is dosed is about 0.001 to about 1000 milligrams.

17. The method of claim 15 wherein the drug is dosed is about 20 to about 300 milligrams.

18. The method of claim 15 wherein said compound is administered to a human.

19. The method of claim 15 wherein said compound is in combination with a pharmaceutically acceptable dilutent or carrier.

\* \* \* \* \*